United States Patent
Kirchhofer et al.

[11] Patent Number: 6,086,567
[45] Date of Patent: Jul. 11, 2000

[54] INJECTION DEVICE

[75] Inventors: Fritz Kirchhofer, Sumiswald; Peter Michel, Burgdorf, both of Switzerland

[73] Assignee: Disetronic Licensing AG, Switzerland

[21] Appl. No.: 08/973,176

[22] PCT Filed: Apr. 2, 1996

[86] PCT No.: PCT/CH96/00116
§ 371 Date: Feb. 26, 1998
§ 102(e) Date: Feb. 26, 1998

[87] PCT Pub. No.: WO97/36626
PCT Pub. Date: Oct. 9, 1997

[51] Int. Cl.[7] .................................................. A61M 5/00
[52] U.S. Cl. ............................................. 604/211; 604/207
[58] Field of Search ..................................... 604/181, 187, 604/207–211

[56] References Cited

U.S. PATENT DOCUMENTS

| 4,592,745 | 6/1986 | Rex et al. . |
| 4,865,591 | 9/1989 | Sams . |

(List continued on next page.)

FOREIGN PATENT DOCUMENTS

| 3638984 | 11/1986 | Denmark . |
| 3645245 | 11/1986 | Denmark . |
| 3900926 | 8/1989 | Denmark . |
| 4223958 | 7/1992 | Denmark . |
| 0037696 | 10/1981 | European Pat. Off. . |
| 0058536 | 8/1982 | European Pat. Off. . |
| 0245312 | 10/1986 | European Pat. Off. . |
| 0268191 | 11/1987 | European Pat. Off. . |
| 0298067 | 6/1988 | European Pat. Off. . |
| B327910 | 1/1989 | European Pat. Off. . |
| A496141 | 1/1991 | European Pat. Off. . |
| 0498737 | 8/1992 | European Pat. Off. . |
| 0516473 | 12/1992 | European Pat. Off. . |
| 0554995 | 8/1993 | European Pat. Off. . |
| 0594349 | 4/1994 | European Pat. Off. . |
| 8702895 | 5/1987 | WIPO . |
| 9110460 | 7/1991 | WIPO . |
| 9218179 | 10/1992 | WIPO . |
| 9305835 | 4/1993 | WIPO . |
| 9316740 | 9/1993 | WIPO . |
| 9409841 | 5/1994 | WIPO . |
| 9415120 | 7/1994 | WIPO . |
| 9501812 | 1/1995 | WIPO . |
| 9504563 | 2/1995 | WIPO . |
| 9607443 | 3/1996 | WIPO . |

*Primary Examiner*—Wynn Wood Coggins
*Assistant Examiner*—Deborah Blyveis
*Attorney, Agent, or Firm*—Dorsey & Whitney LLP

[57] ABSTRACT

The invention relates to an injection device for injecting a selectable dose of a liquid substance from an ampoule, located in an ampoule holder, comprising a piston and a sleeve-shaped mechanism holder, in the interior of which a longitudinally shiftable shaft is provided, the shaft being surrounded by an also longitudinally shiftable advancing sleeve coupled thereto. For selecting a dose of the liquid substance to be injected, a dosing sleeve with a stepped member is provided, the dose to be respectively administered being adjustable by a rotation of the dosing sleeve with the stepped member. The adjusted dose is readable via a dose imprint on the dosing sleeve. The actually possibly administrable dose can be read on a dose scale, fastened to the advancing sleeve, by means of the cooperation of a stop, fastened to the lower end area of the advancing sleeve, with a partition member, fastened to the shaft, the advancing sleeve being, as a result of this mechanism, then no longer movable if the supply of the ampoule is completely used up.

27 Claims, 5 Drawing Sheets

U.S. PATENT DOCUMENTS

| | | |
|---|---|---|
| 4,883,472 | 11/1989 | Michel . |
| 4,946,446 | 8/1990 | Vadher . |
| 4,973,318 | 11/1990 | Holm et al. .............................. 604/208 |
| 5,017,190 | 5/1991 | Simon et al. ........................... 604/207 |
| 5,084,060 | 1/1992 | Freund et al. . |
| 5,114,406 | 5/1992 | Gabriel et al. . |
| 5,279,579 | 1/1994 | D'Amico . |
| 5,279,585 | 1/1994 | Balkwill . |
| 5,292,314 | 3/1994 | D'Alessio et al. . |
| 5,295,976 | 3/1994 | Harris . |
| 5,336,183 | 8/1994 | Greelis et al. . |
| 5,338,311 | 8/1994 | Mahukar . |
| 5,370,629 | 12/1994 | Michel et al. . |
| 5,472,430 | 12/1995 | Vaillancourt et al. . |
| 5,496,293 | 3/1996 | Huggenberger ......................... 604/208 |
| 5,514,097 | 5/1996 | Knauer . |
| 5,527,294 | 6/1996 | Weatherford et al. . |
| 5,549,558 | 8/1996 | Martin . |
| 5,549,575 | 8/1996 | Giambattista et al. . |
| 5,573,510 | 11/1996 | Isaacson . |
| 5,582,598 | 12/1996 | Chanoch . |
| 5,591,136 | 1/1997 | Gabriel . |
| 5,591,138 | 1/1997 | Vaillancourt . |
| 5,593,390 | 1/1997 | Castellano et al. . |
| 5,609,577 | 3/1997 | Haber et al. . |
| 5,643,214 | 7/1997 | Marshall et al. . |
| 5,658,259 | 8/1997 | Pearson et al. . |
| 5,674,204 | 10/1997 | Chanoch . |
| 5,679,111 | 10/1997 | Hjertman et al. . |
| 5,725,508 | 3/1998 | Chanoch et al. . |
| 5,728,074 | 3/1998 | Castellano et al. . |
| 5,743,889 | 4/1998 | Sams . |
| 5,807,346 | 9/1998 | Frezza . | section A-A section B-B

INJECTION DEVICE

RELATED APPLICATIONS

This application claims the priority of PCT application no. PCT/CH96/00116, filed Apr. 2, 1996, which is incorporated herein by reference.

BACKGROUND OF THE INVENTION

1. Field of the Invention

The invention relates to an injection device for injecting a selectable dose of a liquid substance from an ampoule located in an ampoule holder, comprising a sleeve-shaped mechanism holder mechanically coupled thereto, in the interior of the mechanism holder a longitudinally shiftable shaft with a piston disposed thereon being provided which acts on the ampoule, wherein the shaft being surrounded by an also longitudinally shiftable advancing sleeve, mechanically coupled thereto, which in its upper end area is closed by a lid.

2. Description of the Prior Art

An advancing facility for an injection device is known from EP 0 627 229 A1 by means of which a liquid substance from an ampoule can be administered. This advancing device consists of an outer sleeve, an inner sleeve protruding backward from the outer sleeve, and a toothed shaft movable by means of the inner sleeve against the force of a spring. The toothed shaft is provided with teeth, the length of which corresponds to a full injection dose. The inner sleeve is movable forward and backward by the value of the length of a full injection dose between two stops provided on the outer sleeve. The inner sleeve is provided with catching means which lock it in place upon reaching the front position at an opening of the carpoule sleeve, in an unlocking manner with respect to this. Finally, a recoil protection is intended for the toothed shaft.

The injection device provided with this advancing device cannot be employed once more after emptying the carpoule or ampoule.

Another injection device of this kind is known from EP 0 373 321 B1 which consists of an ampoule sleeve for receiving the ampoule and a delivering mechanism. In turn, this is composed of a cylindrical piston shaft with an inner hollow cylinder and an outer hollow cylinder which is formed in one piece with this and that exhibits a guiding cam on its outer shell. A dosing ring is fixed radially to the outer hollow cylinder. The dosing can be read off by means of a scaling fastened to the outer perimeter of the dosing ring through a sight glass set into the housing of the mechanism holder. The delivering mechanism is longitudinally movably arranged in the mechanism holder by means of a retaining spring and secured by a lid screwable into the housing of the mechanism holder. The dosing ring rests against the lid with the force of the retaining spring. The housing of the mechanism holder is provided on its inside with elongated slots of different length in which the corresponding guiding cam of the delivering mechanism is able to glide. As a result, the lift of the delivering mechanism is determined by the length of the elongated slot combining with the guiding cam. The adaptation to the needs of the patients of the dose to be administered exclusively takes place by an authorized person, e.g. a physician. A special-purpose tool is necessary, by means of which an interlocking ring of the device can be unlocked until the guiding cam of the delivering mechanism is released from the respective elongated slot. The physician is then able to select the desired dose by rotation of the released delivering mechanism and renewed catch of the guiding cam into a corresponding elongated slot.

Once selected, the dose cannot be varied without considerable effort. In addition, based on the construction of the delivering mechanism, the injection device can only be used for delivering a single dose although possibly a sufficient supply of medicine is still available in the ampoule. In order to administer another dose of medicine, the ampoule sleeve must be unlocked from the mechanism holder and disposed of together with the ampoule possibly still containing medicine.

An injection device of generic type is known from EP 0 037 696 B1 with which a dose of a liquid substance to be administered can be taken from an ampoule via a transmission mechanism of tractive force effective in one direction upon operating a locking cap. The transmission mechanism of tractive force consists in that one pushing part is equipped with a plurality of teeth and the other pushing part with a pawl, which intermesh and therefore effect the advance of the transmission mechanism of tractive force only in one direction. The maximum lift height and therefore the maximum dose to be administered is limited via a notch and a stop. The operator of the injection device is also able to select less than the maximum dose by listening to the number of clicks which occur when, during the advance, the teeth of the pushing part catch in the pawl. In this connection, one click corresponds to the minimum dose. The operating element, the locking cap, is pushed back up to a stop by means of a spring.

This injection device is designed for extremely careful operation since a click can easily be misheard and different doses to be administered not be safely adjusted. In addition, no display unit is foreseen for the dose to be selected.

Furthermore, the basic problem of these and other injection devices of generic type is that, according to the dose selection, when so to say the last drop which does not correspond to a full dose is still available in the ampoule, this supply is no longer sufficient to fully administer the adjusted dose. Up to now, the operator had no instrument to recognize that this dose, adjusted by him, cannot completely be administered anymore and possibly injected himself with an underdose with serious health consequences.

SUMMARY OF THE INVENTION

Therefore, the problem of the present invention is to provide an injection device with which a variable and simple dose selection with a high operating safety is given, with respect to the fact that a remaining residue in the ampoule does not enable a complete selected dose unit to be administered.

This problem is solved according to the invention in that a dosing sleeve with a stepped member is provided for selecting a dose of a liquid substance to be injected, which is disposed on the mechanism holder in its upper end area, the dose to be respectively administered being adjustable by a rotation of the dosing sleeve with the stepped member, in that the adjusted dose is readable via a dose imprint on a cylindrical part of the dosing sleeve in cooperation with a marking arrow on the mechanism holder, in that the actually possibly administerable dose is readable on a dose scale positioned on the area of the upper end of the advancing sleeve by the cooperation of a stop, disposed on the lower end area of the advancing sleeve, with a partition member disposed on the shaft, and in that the advancing sleeve is no longer movable by means of this mechanism if the supply of the ampoule is completely used up.

DESCRIPTION OF THE PREFERRED EMBODIMENTS

The dosing sleeve is composed thereby of an operating element with a profile, an adjoining cylinder with dose imprint, a catch stop, and the stepped member adjoining this. The constructive coupling of the dosing sleeve to the injection device is characterized in that the dosing sleeve with the stepped member surrounds the advancing sleeve.

The injection device according to the invention has the fundamental advantage that a dose, once adjusted, can be applied repeatedly; the user just has to load the injection device before each injection. The selection of the dose to be applied is conceivably easy due to a simple rotation of the dosing sleeve. Furthermore, this injection device guarantees a safe use until the ampoule is completely emptied.

Further advantageous features of the invention result from the dependent claims.

One embodiment of the invention is represented in the figures.

It is shown in:

Figure 1:
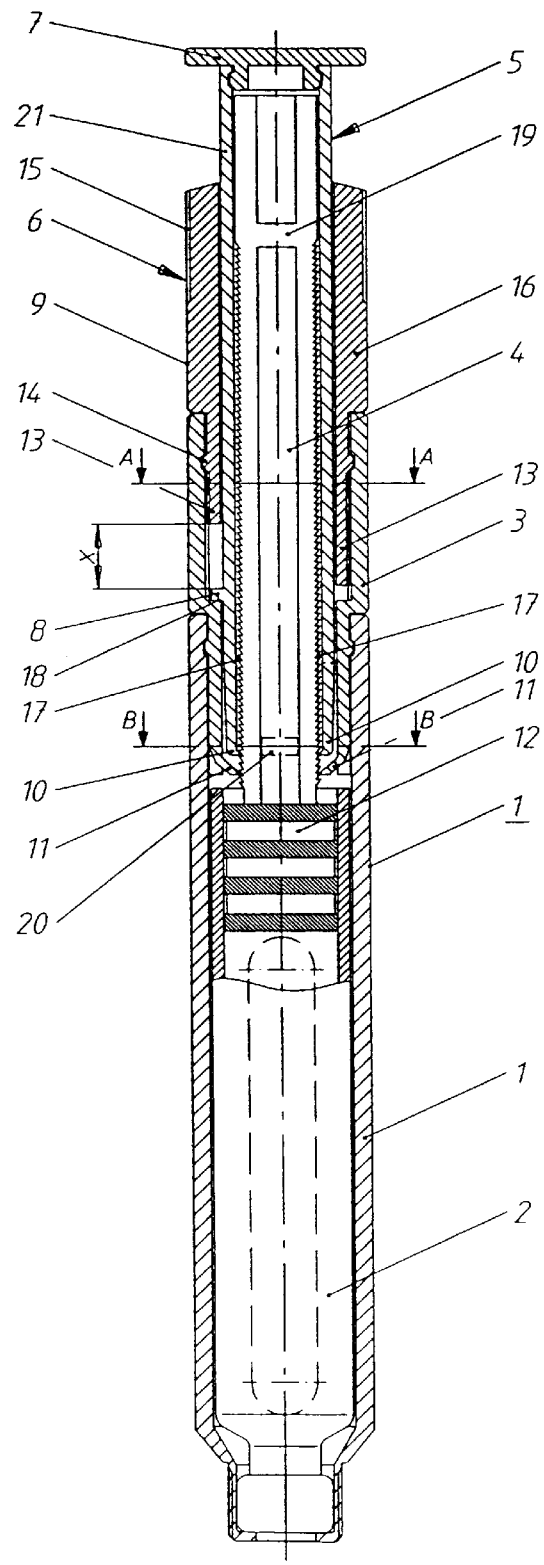
FIG. 1: the injection device according to the invention in section.

The injection device shown in FIG. 1 consists of the ampoule holder 1 in which the ampoule 2 with the piston 12 and with the liquid substance to be administered is located. The sleeve-shaped mechanism holder 3 is mechanically linked to the ampoule holder 1 by a thread or another suitable lock. In the interior of the mechanism holder 3, the longitudinally shiftable shaft 4 is provided acting on the ampoule 2. The shaft 4 is surrounded by an advancing sleeve 5 also longitudinally shiftable and mechanically coupled thereto, which in its upper end area is closed by the lid 7. For selecting a dose of the liquid substance to be injected, the dosing sleeve 6 with the stepped member 13 is provided, which is arranged on the mechanism holder 3 in its upper end area. In this case, the dosing sleeve 6 with the stepped member 13 surrounds the advancing sleeve 5. The dose to be adjusted and to be respectively administered is selectable by a simple rotation of the dosing sleeve 6 with the stepped member 13. The dosing sleeve 6 is mechanically coupled to the mechanism holder 3 via the catch stop 14. The dosing sleeve 6 consists of the profiled operating element 15, the adjoining cylindrical part 16 with the dose imprint 9, the catch stop 14, and the stepped member 13 adjoining this. The adjusted dose is readable in cooperation with the marking arrow 22 placed on the mechanism holder 3. The cam 8 is disposed on the advancing sleeve 5, which upon withdrawing the advancing sleeve 5 in the direction of the lid 7 comes to a stop against the respectively adjusted step of the stepped member 13. Upon pressing down the advancing sleeve 5, the cam 8 comes to a stop against the shoulder 18 of the mechanism holder 3 resulting in the injection lift X. For the mechanical coupling of shaft 4 and the advancing sleeve 5 the shaft 4 is provided with the two toothings 17 at opposite sides, which (17) cooperate with the locking cam 10 of the advancing sleeve 5. In this case, the depth of tooth of the toothings 17 on the shaft 4 corresponds to the step height of the stepped member 13. In the area of its lower end, the mechanism holder 3 comprises the catches 11 which also cooperate with the toothings 17 of the shaft 4. The selectable dose, adjusted by means of the dosing sleeve 6 with the stepped member 13, cannot possibly be completely administered if the residual supply in the ampoule 2 is insufficient. In order to clarify which quantitative amount of the liquid substance can still actually be administered, the actually possibly administerable dose is readable (FIG. 3) on the dose scale 21 placed on the advancing sleeve 5 in its upper end area by the cooperation of the stop 20, 20', disposed on the lower end area of the advancing sleeve 5, with the partition member 19, 19' disposed on the shaft 4. By means of this mechanism the advancing sleeve 5 is no longer movable if the supply of the ampoule 2 is completely used up. As a rule, the dose, selected by means of the dosing sleeve and read off by means of the dose imprint 9, corresponds completely to the possible dose to be administered read off on the dose scale 21. But in case that upon decreasing ampoule supply, this supply is not sufficient to completely administer the adjusted and selected dose, this deficiency can be made visible by means of the dose scale 21 in that the advancing sleeve 5 can only still be pulled out a fraction of the value for the loading which otherwise would be possible for a full dose. The operator recognizes this from a discrepancy of the read off dose adjustment of the dosing sleeve over the read-off dose imprint 9 and the display on the dose scale 21 which in this case is always smaller.

Figure 4:
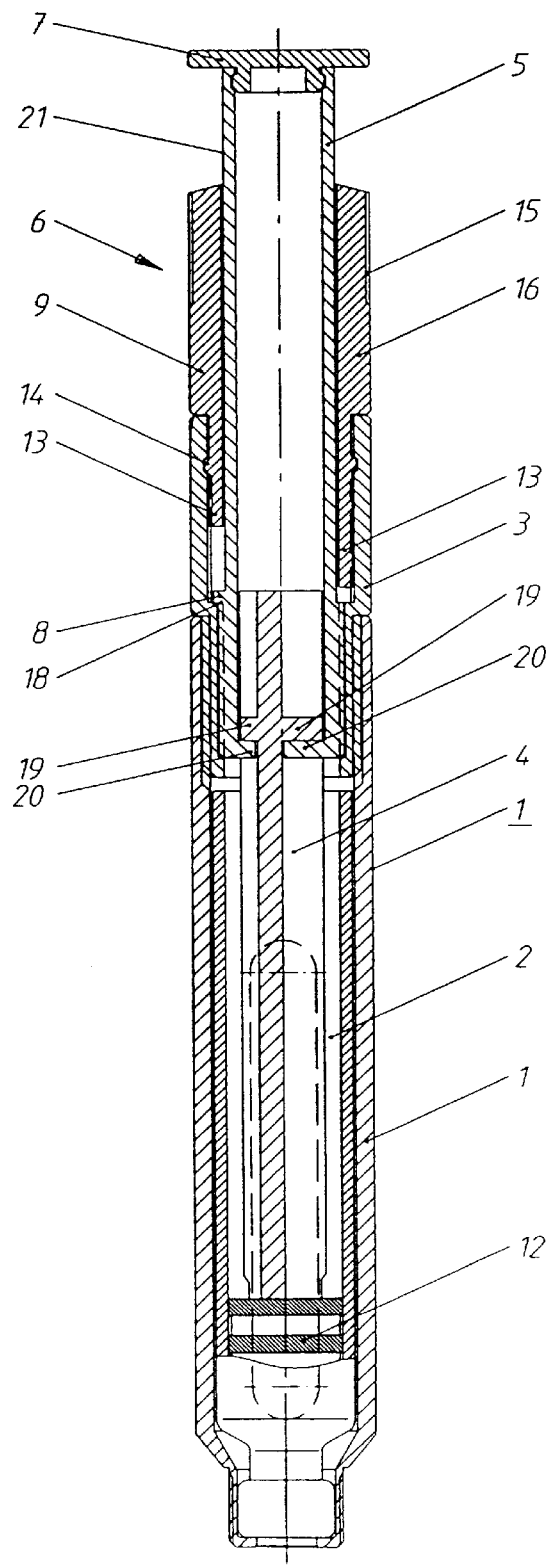
FIG. 4: the injection device in section according to FIG. 2 with shaft in the end stop.
Figure 5:
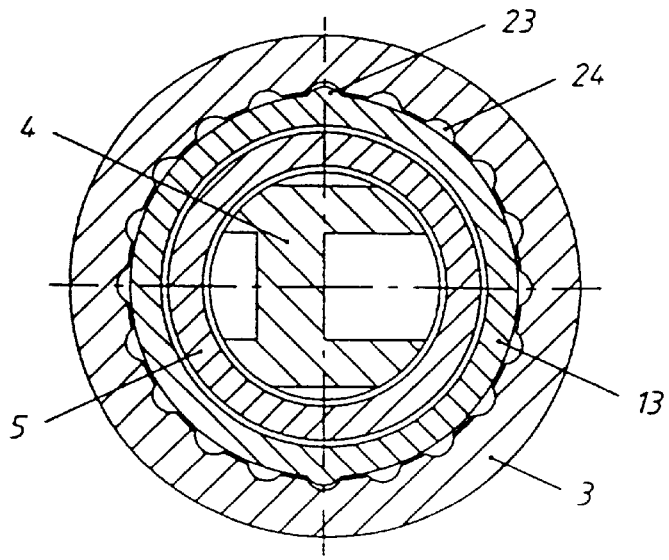
FIG. 5: a sectional view along the line A—A in FIG. 1.
Figure 6:
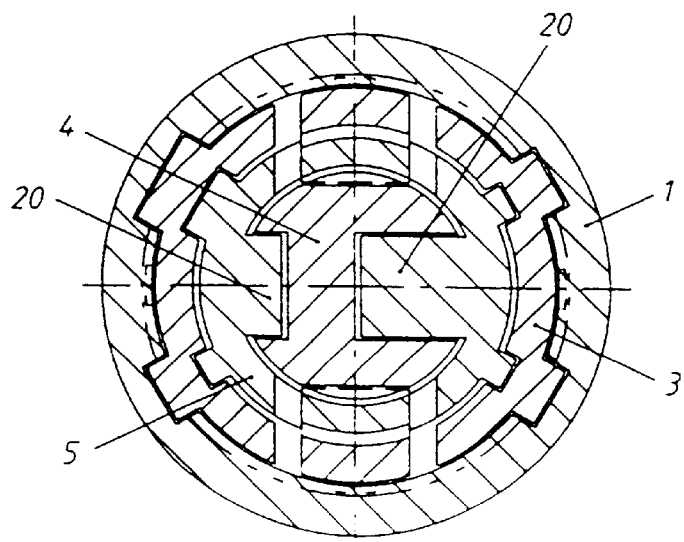
FIG. 6: a sectional view along the line B—B in FIG. 1.

The mode of operation of the injection device according to the invention is as follows:

The operator turns the dosing sleeve 6 with the stepped member 13 until the desired dose imprint 9 is shown by the marking arrow 22. Then, the injection device is loaded. FIG. 1 shows this before the loading. For the loading, the advancing sleeve 5 is pulled upward by the lid 7, mechanically coupled thereto, until the cam 8, which is part of the advancing sleeve 5, comes to a stop against the currently adjusted step of the stepped member 13. In this case, the locking cams 10 of the advancing sleeve 5 glide over the toothings 17 of the shaft 4 which teeth (not shown) are arrow-shaped downwardly. In order to prevent that the shaft 4 is nevertheless shifted upward at the same time, the catches 11 are provided on the mechanism holder 3 which is not longitudinally shiftable. Thus, the catches 11 brace themselves into the toothings 17 and prevent a motion of the shaft 4 upward. For administering the selected dose, pressure in the downward direction is exerted by the operator on the lid 7 and on the advancing sleeve 5 coupled thereto. In this case, the locking cams 10 brace themselves into the toothings 17 and, so to say, take the shaft 4 along and the piston 12 coupled to the shaft 4 exerts pressure on the ampoule 2 located in the ampoule holder 1, with which the liquid substance is applied by administering it through an injection needle (not shown). Upon pressing down the advancing sleeve 5 by means of the lid 7, the teeth of the toothings 17 also glide over the catches 11 of the mechanism holder 3, wherein these are out of mesh by means of the selected arrow-shape of the teeth of the toothings 17. The advance motion of the advancing sleeve S in the downward direction lasts until the cam 8 comes to a stop against the shoulder 18 of the mechanism holder 3 so that the selected dose of the liquid substance is administered. The injection device is prepared by renewed loading for one or more subsequent injections. The shaft 4 remains during the loading processes in the immediately before-given state by means of the toothing of catches 11 with the teeth of the toothings 17. In particular, the shaft 4 moves only in one direction, namely downward, while the advancing sleeve 5 lets itself move in two directions, namely upward for loading and downward for administering. This bidirectional longitudinal shiftability of the advancing sleeve comes up against a limit if, as shown in FIG. 4, the supply of the ampoule 2 is completely used up by the immediately preceding injection. At this time, the partition member 19, 19' and the stop 20, 20' are completely in contact with each other. A pulling back of the advancing sleeve 5 for a renewed loading process is no longer possible. In this way, it is prevented that a further injection with possibly serious health consequences can occur if the ampoule is empty. For the case that, according to the dose selection, the supply in the ampoule 2 is only sufficient for a fraction, due to the fact that the ampoule 2 is nearly empty, the dose scale 21, placed on to the advancing sleeve 5, is provided. Due to the previously described mechanism with the partition member 19, 19' and the cooperation with the stop 20, 20', the advancing sleeve can in this case only be pulled out to a fraction of a fully adjusted dose for the loading until the stop 20, 20' comes to a stop by the partition member 19, 19'. A smaller value of dose amount to be administered appears on the dose scale 21 than is readable from the dose imprint 9 by means of the marking arrow 22. With the dose scale 21 the upper edge of the operating element 15 serves as a reading mark. The user recognizes by this discrepancy that the residual amount still available in the ampoule does not correspond to a full selected dose, and he can therefore avoid possibly serious health consequences. The shaft 4, according to the FIGS. 5 and 6, shows essentially an H-shaped cross-section. In its interior the mechanism holder 3 shows numerous bulges 24 into which the projections 23 of the stepped member 13 catch (FIG. 5). The length of the injection lift X is determined by the individual differences of the steps of the stepped member 13 such that X is an integral multitude of a dose unit, with an ampoule 2 with a given diameter. Furthermore, the partition member 19, 19' is disposed on the shaft 4 in such a manner that, upon its resting against the stop 20, 20', the ampoule 2 is completely emptied.

Figure 2:
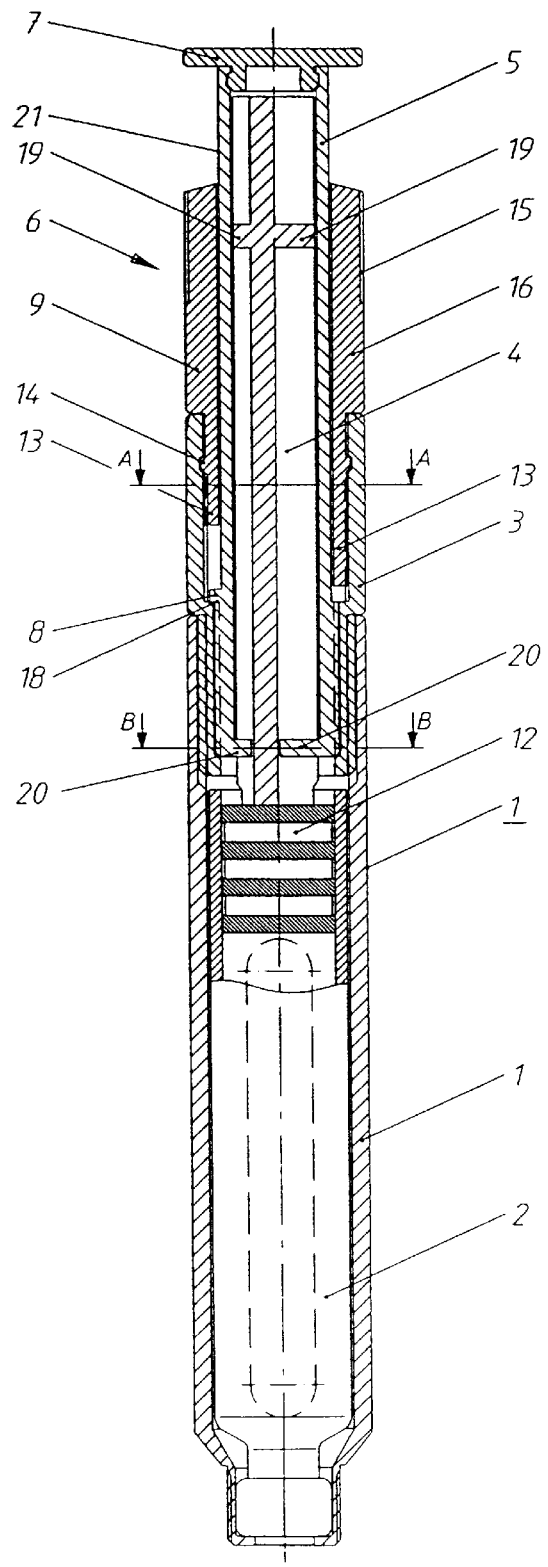
FIG. 2: the injection device in a sectional view which is rotated by 90 degrees in comparision to the view shown in FIG. 1.
Figure 3:
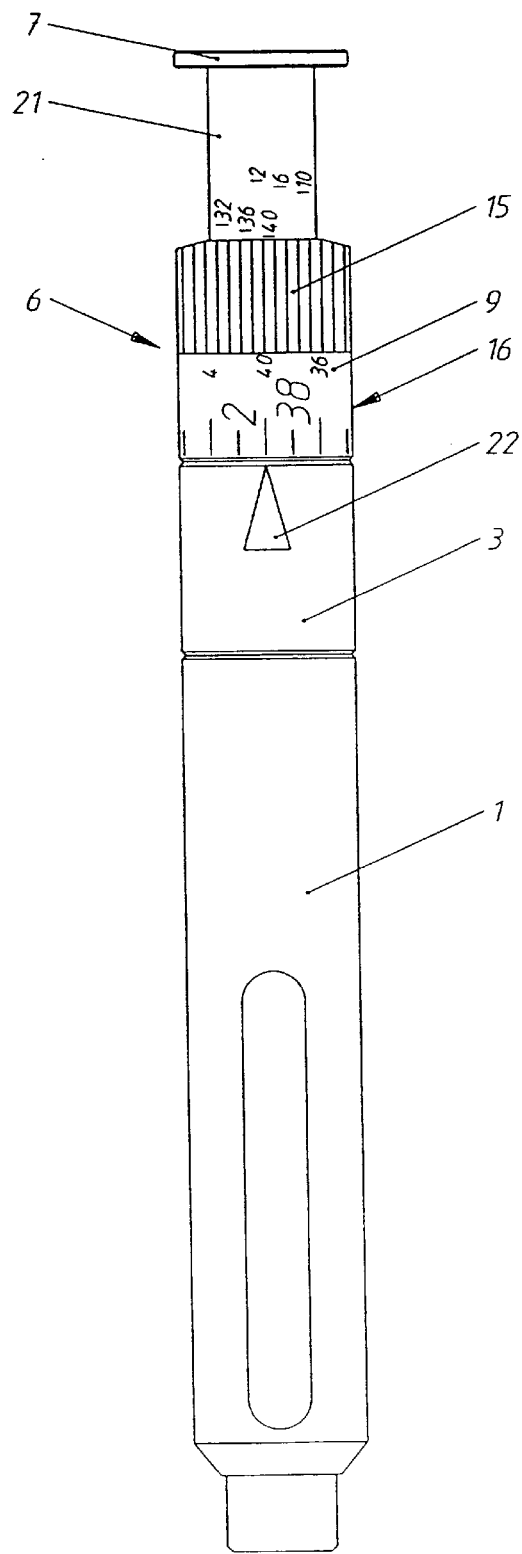
FIG. 3: the injection device in frontal view.

The FIG. 2 shows the injection device in a sectional view which is turned at 90 degrees with respect to the view shown in FIG. 1. In this case, all reference symbols are identical to those of FIG. 1. FIG. 3 shows the injection device in frontal view. FIG. 4 shows a section, according to FIG. 2, with the shaft 4 at the end stop by the resting of partition member 19, 19' against the stop 20, 20' so that the advancing sleeve 5 can no longer be pulled backward for the loading. FIG. 5 shows a sectional view along the line A—A in FIG. 1. In this case, the H-shaped cross-section of the shaft 4 is clearly apparent. FIG. 6 shows a sectional view along the line B—B in FIG. 1. In this case, it is to be recognized how the stop 20, 20' cooperates with the shaft 4 H-shaped in the cross-section.

The injection device according to the invention can serve for administering medicines. Lotions and other liquid substances can also be administered with it.

We claim:

1. An injection device for injecting a selectable dose of a liquid substance from an ampoule located in an ampoule holder, said injection device comprising a sleeve-shaped mechanism holder coupled to the ampoule holder, a longitudinally shiftable shaft in the mechanism holder for acting on the ampoule, the shaft being surround by an also longitudinally shiftable advancing sleeve having an upper end area closed by a lid, said injection device further comprising:

A) a dosing sleeve operably coupled to the mechanism holder for selecting a dose to be injected;
B) a dose imprint on a cylindrical portion of the dosing sleeve and a marking arrow on the mechanism holder for displaying the selected dose; and
C) a dose scale provided in the area of the upper end of the advancing sleeve for displaying an actually possibly administrable dose.

2. The injection device according to claim 1, wherein the displaying provided by the dose scale is produced by the cooperation of a stop disposed on the lower end of the advancing sleeve and a partition member disposed on the shaft, the cooperation also making the advancing sleeve immobile if the ampoule is empty.

3. The injection device according to claim 1, wherein the dosing sleeve comprises a stepped portion.

4. The injection device according to claim 3, wherein the dosing sleeve is generally adjacent to one end of the mechanism holder, and wherein the dose to be administered is selectable by rotation of the dosing sleeve.

5. The injection device according to claim 3, wherein a cam associated with the advancing sleeve contacts a selected step of the stepped portion upon pulling out the advancing sleeve and, upon pressing down the advancing sleeve, the cam contacts a shoulder of the mechanism holder, resulting in an injection lift of a selected magnitude.

6. The injection device according to claim 3, wherein the dosing sleeve comprises an operating element with a profile, a cylindrical part adjacent to the operating element and having a dose imprint, and a catch stop.

7. The injection device according to claim 3, the mechanism holder further comprising a surface which the stepped portion engages.

8. The injection device according to claim 1, wherein the dosing sleeve generally surrounds the advancing sleeve.

9. The injection device according to claim 1, wherein the shaft and advancing sleeve are operably coupled by teeth carried by the shaft and cams carried by the advancing sleeve.

10. The injection device according to claim 9, the mechanism holder further comprising two catches adjacent to one end, said catches operably cooperating with the shaft.

11. The injection device according to claim 3, wherein the stepped portion comprises a plurality of steps each having a step height, and wherein the depth of the teeth on the shaft generally corresponds to the step height.

12. The injection device according to claim 1, the shaft being generally H-shaped in cross-section.

13. The injection device according to claim 1, wherein the device is for administering medicine.

14. An injection device for injecting a selectable dose of a substance comprising an ampoule holder for holding an ampoule containing the substance and a mechanism holder operably coupled to the ampoule holder, wherein the mechanism holder generally contains a longitudinally shiftable shaft generally surrounded by a longitudinally shiftable advancing sleeve, the injection device further comprising a dosing sleeve generally surrounding a portion of the advancing sleeve for selecting a dose, and a dose reader comprising a dose imprint carried by the dosing sleeve and a mark carried on the mechanism holder, whereby a selected dose is readable, the injection device further comprising a stop carried on the advancing sleeve and a cooperating partition member carried on the shaft, whereby the advancing sleeve is movable and not movable depending on the amount of the substance in the ampoule.

15. The injection device according to claim 14, wherein the shaft and advancing sleeve are operably coupled by teeth carried by the shaft and cams carried by the advancing sleeve.

16. The injection device according to claim 15, wherein the dosing sleeve comprises an operating element with a profile, a cylindrical part adjacent to the operating element and carrying the dose imprint, and a catch stop.

17. A method of avoiding the injection of an improper dose of a substance from an injection device, said method comprising providing two dose information sites on the injection device and comparing the information provided by the two sites, whereby if there is a discrepancy between the information displayed by the sites, injection should be avoided.

18. The method according to claim 17, wherein one site is a selected dose display site and the other site is a residual substance display site.

19. The method according to claim 18, wherein a user manipulates a portion of the injection device to select a dose to be injected, information about the selected dose being displayed automatically at the selected dose display site, and wherein a user loads the injection device after selecting a dose to be injected, information about the residual substance in the injection device being displayed automatically at the residual substance display site.

20. A method for avoiding the injection of a partial dose of a substance, said method comprising the steps of:

providing an injection device with a dose imprint for selecting a dose and displaying information about a selected dose;

providing the injection device with a dose scale for displaying the actual amount of substance available for the selected dose; and comparing the dose imprint to the dose scale whereby, if the dose displayed by the dose scale is less than the dose displayed by the dose imprint, injection should be avoided.

21. An injection device for injecting a dose of a substance, said device comprising two dose information sites on the injection device, wherein one site is a selected dose display site and the other site is a residual substance display site.

22. The apparatus according to claim 21, wherein a user manipulates a portion of the injection device to select the dose to be injected, information about the selected dose being displayed automatically at the selected dose display site, and wherein a user loads the injection device after selecting the dose to be injected, information about the amount of substance in the injection device being displayed automatically at the residual substance display site.

23. A dosing sleeve for an injection device including an injectable substance holding portion and an injection mechanism portion operably coupled to the injectable substance holding portion, the injection mechanism portion including a shaft and an advancing sleeve operably coupled to the shaft, said dosing sleeve operably coupled to the advancing sleeve and comprising a generally cylindrical sleeve body with a profiled portion adjacent to a first end, a generally medial cylindrical portion, a catch stop and a stepped portion adjacent to a second end.

24. The dosing sleeve according to claim 23, further comprising a dose imprint in the cylindrical portion.

25. The dosing sleeve according to claim 23, wherein the dosing sleeve is generally adjacent to one end of the injection mechanism portion, and wherein the dose to be administered is selectable by rotation of the dosing sleeve.

26. The dosing sleeve according to claim 23, wherein the dosing sleeve generally surrounds the advancing sleeve.

27. The dosing sleeve according to claim 23, wherein a cam associated with the advancing sleeve contacts a selected step of the stepped portion when the advancing sleeve is moved in one axial direction and, when the advancing sleeve is moved in the opposite axial direction, the cam contacts a shoulder of the injection mechanism portion, resulting in an injection lift of a selected magnitude.

* * * * *